United States Patent [19]

Singh

[11] 4,444,580

[45] Apr. 24, 1984

[54] N-SUBSTITUTED N-(PHOSPHONOMETHYL)AMINOETHANAL DERIVATIVES AS HERBICIDES

[75] Inventor: Rajendra K. Singh, Maryland Heights, Mo.

[73] Assignee: Monsanto Company, St. Louis, Mo.

[21] Appl. No.: 437,985

[22] Filed: Nov. 1, 1982

[51] Int. Cl.³ .......................... A01N 57/20; C07F 9/40
[52] U.S. Cl. .......................................... 71/86; 260/944
[58] Field of Search ............................ 260/944; 71/86

[56] References Cited

U.S. PATENT DOCUMENTS

| 3,970,695 | 7/1976 | Rueppet ................................ 71/86 |
| 4,180,394 | 12/1979 | Franz et al. ............................ 71/86 |
| 4,218,235 | 8/1980 | Franz et al. ............................ 71/86 |

FOREIGN PATENT DOCUMENTS 1482342  8/1977  United Kingdom .

Primary Examiner—Anton H. Sutto
Attorney, Agent, or Firm—David Bennett; Richard H. Shear; Arnold H. Cole

[57] ABSTRACT

Certain N-trifluoroacetyl derivatives of N-substituted N-(phosphonomethyl)aminoethanal derivatives are described which display post-emergent herbicidal activity particularly against broadleaf weeds.

7 Claims, No Drawings

N-SUBSTITUTED N-(PHOSPHONOMETHYL)AMINOETHANAL DERIVATIVES AS HERBICIDES

BACKGROUND OF THE INVENTION

This invention relates to novel compounds that are useful as post-emergent herbicides, particularly against broadleaf weeds. The compounds are derivatives of N-phosphonomethylglycine which is itself an efficient non-selective post-emergent herbicide as is fully described in U.S. Pat. No. 3,799,758.

The systemic herbicidal activity of a compound is often not readily predictable, largely because the precise mode of operation of systemic herbicides is not fully understood. It is, therefore, difficult to predict which combination of functional groups will be effective.

A small group of compounds has now been identified which, unlike a number of closely related compounds, displays post-emergent herbicidal activity especially against broadleaf weeds.

DESCRIPTION OF THE INVENTION

The novel compounds of the invention have the generic formula:

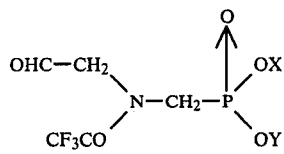

where X and Y are each halo-substituted or unsubstituted aryl or alkaryl groups. The preferred group is phenyl but one or both of X and Y can be, for example, a chlorophenyl, dichlorophenyl, tolyl or naphthyl group.

A preferred method of preparing the novel compounds of the invention comprises reacting a diaryl phosphite (the aryl group being chosen to provide X and Y in the above formula) with 1,3,5-triallylhexahydrosymtriazine in acetonitrile at a temperature of about 25° C. to give N-phosphonomethylallylamine. This is then reacted with trifluoroacetic anhydride usually at about 0°–5° C. in methylene dichloride and in the presence of a proton acceptor such as triethylamine to bring about substitution on the nitrogen of the allylamine group with a trifluoroacetyl group. The compound of the invention may be generated from this intermediate compound by oxidation to the aldehyde by the action of ozone at a temperature below −50° C. and preferably at about −70° to −80° C. in an alcohol solvent such as methanol.

DESCRIPTION OF PREFERRED EMBODIMENTS

The invention is now further described with reference to the following Examples which are for the purpose of illustration only and are intended to imply no limitation on the essential scope of the invention.

EXAMPLE 1

This example illustrates a method of preparing a compound of the invention having the formula:

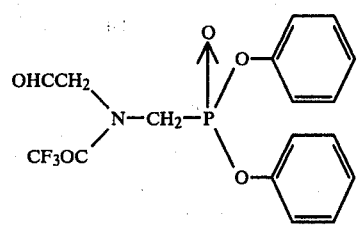

Allylamine (1 mole) was mixed with 50 ml of ethanol in a reaction vessel, placed in a water bath, and 1 mole of formaldehyde (as a 37% aqueous solution) was added with stirring at such a rate that the temperature did not exceed 30° C. The stirred mixture was allowed to stand for two days and then concentrated to remove ethanol. The mixture was then diluted with 200 ml of ether and washed with water, brine, and finally dried over magnesium sulfate. After removal of solvent, 82.39 g of an oil with the empirical formula $C_{12}H_{21}N_3$ remained. This oil was identified as 1,3,5-triallylhexahydro-symtriazine by its proton magnetic resonance spectrum in deuterochloroform.

This reaction product (0.2 mole, 13.8 g) was mixed with an equimolar amount (52.0 g) of diphenyl phosphite in 200 ml of acetonitrile and the mixture was allowed to stand overnight at room temperature. The solvent was then removed to give 65.96 g of the reaction product, N-(diphenylphosphonomethyl)allylamine. The product (18.18 g, 0.06 mole) was then reacted with 0.12 mole (25.2 g) of trifluoroacetic anhydride and triethylamine (0.13 mole, 13.13 g) in 225 ml of dichloromethane. This reaction placed a trifluoroacetyl substituent on the amine group and yielded 22.8 g of this derivative.

The compound of the invention was obtained from this final intermediate by bubbling ozone through a solution of 4.18 g (0.0104 mole) of the intermediate dissolved in 200 ml of methanol for about 5 minutes at about −78° C. At this point, the solution had turned blue. Dimethyl sulfide (2 ml) was added and the solution was allowed to warm to room temperature.

After six hours, a further 2 ml of dimethyl sulfide was added and the reaction mixture was allowed to stand for a further 1.5 hours. This yielded the crude aldehyde product in methanolic solution. This solution was concentrated, diluted with 200 ml of dichloromethane, washed with water three times, then dried over sodium sulfate for a few minutes. The dried reaction mixture was then left in a refrigerator overnight. Next day, the solvent was removed to yield 4.5 g of product which was purified by column chromatography on silica gel and the product was eluted with a 50/50 (by volume) mixture of cyclohexane and ethyl acetate. The purified product, the diphenyl ester of [(2-oxoethyl)(trifluoroacetyl)amino]methyl phosphonic acid, was obtained in 41% theoretical yield and was shown to have the structure given above by the use of a proton nuclear magnetic resonance analysis.

EXAMPLE 2

This Example shows the post-emergent activity of the compound produced in Example 1 and indicates by the use of comparative data the surprising nature of the discovery of this activity.

A 10% solution in tetrahydrofuran of the compound produced in Example 1 was formulated into a spray solution comprising 3 parts of cyclohexanone and 1 part of a surfactant (35 parts of the butylamine salt of dodecylbenzenesulfonic acid and 65 parts of tall oil condensed with ethylene oxide in the ratio of 11 moles of ethylene oxide to 1 mole of tall oil). This spray was then applied to two week old plants of the indicated species in amounts sufficient to give the indicated application rates. The plants were then placed in a greenhouse and left under good growing conditions for four weeks. The condition of the plants was observed after two and four weeks and a determination made of the extent to which they had been injured. This was translated to a code as follows:

0-24% injured—0
25-49% injured—1
50-74% injured—2
75-99% injured—3
100% killed—4

The plants treated and the code letter assigned to them were as follows:

| | |
|---|---|
| Canadian Thistle | A |
| Cockleburr | B |
| Velvetleaf | C |
| Morning Glory | D |
| Lambsquarters | E |
| Smartweed | F |
| Nutsedge | G |
| Quackgrass | H |
| Johnsongrass | I |
| Brome-Cheat | J |
| Barnyardgrass | K |
| Soybean | L |
| Sugar Beet | M |
| Wheat | N |
| Rice | O |
| Sorghum | P |

The herbicidal activity of the compound under test was as shown in Table I.

TABLE I

| Application Rate (kg/ha) | Observation (Weeks after Treatment) | Broad Leaf Weeds A B C D E F | Narrow-leaf Weeds G H I J K | Crop Plants L M N O P |
|---|---|---|---|---|
| 11.2 | 2 | 1 2 2 2 3 2 | 1 1 1 1 1 | — — — — — |
|  | 4 | 2 1 2 2 4 4 | 0 0 1 0 2 | — — — — — |
| 5.6 | 2 | 1 3 1 1 2 4 | 0 0 0 0 2 | 1 0 0 0 1 |
|  | 4 | 1 4 1 1 3 4 | 0 0 0 0 2 | 1 1 1 0 1 |

It would appear that in the main, the herbicidal activity of the compound is directed against broadleaf weeds with relatively little injury being done to crops or narrow-leaf weeds.

From illustrative data presented above, it should be clear that the herbicidal response will be dependent upon the compound employed, the rate of application, the plant specie involved, and other factors well understood by those skilled in the art.

The herbicidal compositions (including concentrates which require dilution prior to application to the plants) of this invention contain at least one active ingredient and an adjuvant in liquid or solid form. The compositions are prepared by admixing the active ingredient with an adjuvant such as a diluent, extender, carrier, or conditioning agent to provide composition in the form of a finely-divided particulate solid, pellet, solution, dispersion, or emulsion. Thus, the active ingredient can be used with an adjuvant such as a finely-divided solid, a liquid of organic orgin, water, a wetting agent, a dispersing agent, an emulsifying agent, or any suitable combination of these. From the viewpoint of economy and convenience, water is the preferred diluent. However, it is found that the compounds of the invention are susceptible to hydrolysis in aqueous media and, in some cases, this may dictate the use of non-aqueous solvent media such as tetrahydrofuran.

The herbicidal compositions of this invention, particularly liquids and soluble powders, preferably contain as a conditioning agent, one or more surface-active agents in amounts sufficient to render a given composition readily dispersible in water or in oil. The incorporation of a surface-active agent into the compositions greatly enhances their efficacy. By the term "surface-active agent" it is understood that wetting agents, dispersing agents, suspending agents, and emulsifying agents are included therein. Anionic, cationic, and non-ionic agents can be used with equal facility.

Preferred wetting agents are alkyl benzene and alkyl naphthalene sulfonates, sulfated fatty alcohols, amines or acid amides, long-chain acid esters of sodium isothionate, esters of sodium sulfosuccinate, sulfated or sulfonated fatty acid esters, petroleum sulfonates, sulfonated vegetable oils, ditertiary acetylenic glycols, polyoxyethylene derivatives of alkylphenols (particularly isooctylphenol and nonylphenol) and polyoxyethylene derivatives of the mono-higher fatty acid esters of hexitol anhydrides (e.g., sorbitan). Preferred dispersants are methyl cellulose, polyvinyl alcohol, sodium lignin sulfonates, polymeric alkyl naphthalene sulfonates, sodium naphthalene sulfonate, polymethylene bisnaphthalene sulfonate, and sodium N-methyl-N- (long-chain acid) laurates.

Solvent-dispersible powder compositions can be made containing one or more active ingredients, an inert solid extender, and one or more wetting and dispersing agents. The inert solid extenders are usually of mineral origin such as the natural clays, diatomaceous earth, and synthetic minerals derived from silica and the like. Examples of such extenders include kaolinites, attapulgite clay, and synthetic magnesium silicate. Dispersible powders of this invention usually contain from about 5 to 95 parts by weight of active ingredient, from 0.25 to 25 parts by weight of wetting agent, from 0.25 to 25 parts by weight of dispersant, and from 4.5 to about 94.5 parts by weight inert solid extender, all parts being by weight of the total composition. Where required, from about 0.1 to 2.0 parts by weight of the solid inert extender can be replaced by a corrosion inhibitor or anti-foaming agent or both.

Suspensions can be prepared by mixing together and grinding a slurry of an insoluble active ingredient in the presence of a dispersing agent to obtain a concentrated slurry of very finely-divided particles. The resulting concentrated suspension is characterized by its extremely small particle size, so that when diluted and sprayed, coverage is very uniform.

Emulsifiable oils are usually solutions of active ingredient in water-immiscible or partially water-immiscible solvents together with a surface-active agent. Suitable solvents for the active ingredient of this invention include hydrocarbons and water-immiscible ethers, esters, or ketones. The emulsifiable oil compositions generally contain about 5 to 95 parts active ingredient, about 1 to 50 parts surface-active agent, and about 4 to 94 parts solvent, all parts being by weight based on the total weight of emulsifiable oil.

Compositions of this invention can also contain other additaments, for example, fertilizers, phytotoxicants and plant growth regulants, pesticides, and the like used as adjuvants or in combination with any of the above-described adjuvants. The compositions of this invention can also be admixed with the other materials, e.g., fertilizers, other phytotoxicants, etc., and applied in a single application. Chemicals useful in combination with the active ingredients of this invention either simultaneously or sequentially include, for example, triazines, ureas, carbamates, acetamides, acetanilides, uracils, acetic acids, phenols, thiolcarbamates, triazoles, benzoic acids, nitriles, and the like such as:

3-amino-2,5-dichlorobenzoic acid
3-amino-1,2,4-triazole
2-methoxy-4-ethylamino-6-isopropylamino-s-triazine
2-chloro-4-ethylamino-6-isopropylamino-s-triazine
2-chloro-N,N-diallylacetamide
2-chloroallyl diethyldithiocarbamate
N'-(4-chlorophenoxy)phenyl-N,N-dimethylurea
1,1-dimethyl-4,4'-bipyridinium dichloride
isopropyl m-(3-chlorophenyl)carbamate
2,2-dichloropropionic acid
S-2,3-dichloroallyl N,N-diisopropylthiolcarbamate
N,N-diisopropylthiolcarbamate
2-methoxy-3,6-dichlorobenzoic acid
2,6-dichlorobenzonitrile
N,N-dimethyl-2,2-diphenylacetamide
6,7-dihydrodipyrido(1,2,-a:2',1'-c)-pyrazidinium salt
3-(3,4-dichlorophenyl)-1,1-dimethylurea
4,6-dinitro-o-sec-butylphenol
2-methyl-4,6-dinitrophenol
ethyl N,N-dipropylthiolcarbamate
2,3,6-trichlorophenylacetic acid
5-bromo-3-isopropyl-6-methyluracil
3-(3,4-dichlorophenyl)-1-methoxy-1-methylurea
2-methyl-4-chlorophenoxyacetic acid
3-(p-chlorophenyl)-1,1-dimethylurea
1-butyl-3-(3,4-dichlorophenyl)-1-methylurea
N-1-naphthylphthalamic acid
1,1'-dimethyl-4,4'-bipyridinium salt
2-chloro-4,6-bis(isopropylamino)-s-triazine
2-chloro-4,6-bis(ethylamino)-s-triazine
2,4-dichlorophenyl-4-nitrophenyl ether
alpha, alpha, alpha-trifluoro-2,6-dinitro-N,N-dipropyl-p-toluidine
S-propyl dipropylthiolcarbamate
2,4-dichlorophenoxyacetic acid
N-isopropyl-2-chloroacetanilide
2',6'-diethyl-N-methoxymethyl-2-chloroacetanilide
monosodium acid methanearsonate
disodium methanearsonate
N-(1,1-dimethylpropyl)-3,5-dichlorobenzamide.

Fertilizers useful in combination with the active ingredients include, for example, ammonium nitrate, urea, potash, and superphosphate.

When operating in accordance with the present invention, effective herbicidal amounts of the compositions are applied directly or indirectly to the plants. The application of liquid and particulate solid plant regulating compositions can be carried out by conventional methods, e.g., power dusters, boom and hand sprayers, and spray dusters. The compositions can also be applied from airplanes as a dust or a spray because of their effectiveness at low dosages.

The application of a herbicidally-effective amount of the compounds of this invention to the plant is an important aspect of the practice of the present invention. The exact amount of active ingredient to be employed is dependent upon the response desired in the plant as well as such other factors as the plant species, and the environmental conditions, as well as the specific compound employed. In general, the active ingredients are employed in herbicidally-effective amounts equivalent to from about 2 to about 15.0 kg/hectare.

Although the invention is described with respect to specific embodiments, the details thereof are not to be construed as limitations except to the extent indicated in the following claims.

What is claimed is:

1. An N-(phosphonomethyl)aminoethanal derivative having the formula:

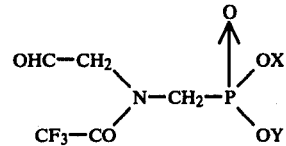

wherein X and Y are each individually selected from the group consisting of $C_6$ to $C_{10}$ aryl and alkaryl radicals and halogen-substituted equivalents of the same radicals.

2. An N-(phosphonomethyl)aminoethanal derivative according to claim 1 in which X and Y each represent the same group.

3. An N-(phosphonomethyl)aminoethanal derivative according to claim 1 which X and Y are both phenyl.

4. A method of controlling broadleaf weeds which comprises applying to the weeds a herbicidally effective amount of an N-(phosphonomethyl)aminoethanal derivative according to claim 1.

5. A herbicidal method according to claim 4 in which the N-(phosphonomethyl)aminoethanal derivative is the diphenyl ester of [(2-oxoethyl)(trifluoroacetyl)amino]methyl, phosphonic acid.

6. A composition comprising from 5 to 95% by weight of a herbicidally-effective amount of an N-(phosphonomethyl)aminoethanal derivative according to claim 1 and from 95 to 5% by weight of an adjuvant.

7. A composition comprising from 5 to 95% by weight of a herbicidally-effective amount of the diphenyl ester of [(2-oxoethyl)(trifluoroacetyl)amino]methyl, phosphonic acid and from 95 to 5% by weight of an adjuvant.

* * * * *